US008755896B2

(12) United States Patent
Humayun et al.

(10) Patent No.: US 8,755,896 B2
(45) Date of Patent: Jun. 17, 2014

(54) TREATMENT OF CONSUMPTION DISORDERS WITH BIOSTIMULATION

(75) Inventors: Mark Humayun, Glendale, CA (US); Sean Caffey, Manhattan Beach, CA (US); Jeff Brennan, Los Angeles, CA (US)

(73) Assignee: University of Southern California, Los Angeles, CA (US)

(*) Notice: Subject to any disclaimer, the term of this patent is extended or adjusted under 35 U.S.C. 154(b) by 934 days.

(21) Appl. No.: 12/025,454

(22) Filed: Feb. 4, 2008

(65) Prior Publication Data

US 2008/0221642 A1 Sep. 11, 2008

Related U.S. Application Data

(60) Provisional application No. 60/888,124, filed on Feb. 5, 2007.

(51) Int. Cl.
A61N 1/36 (2006.01)
(52) U.S. Cl.
USPC .................................. 607/58; 607/2; 607/134
(58) Field of Classification Search
USPC ................................................ 607/2, 58, 134
See application file for complete search history.

(56) References Cited

U.S. PATENT DOCUMENTS 5,540,734 A * 7/1996 Zabara ............................. 607/46
5,792,210 A 8/1998 Wamubu et al.
6,954,668 B1 * 10/2005 Cuozzo .............................. 607/2
7,062,320 B2 6/2006 Ehlinger, Jr.
7,167,750 B2 1/2007 Knudson et al.
7,317,948 B1 * 1/2008 King et al. ....................... 607/62
2003/0176892 A1 9/2003 Shalev
2007/0093870 A1 * 4/2007 Maschino ........................ 607/2

FOREIGN PATENT DOCUMENTS

| JP | S62501192 A | 5/1987 |
| JP | 2004522526 A | 7/2004 |
| JP | 2006521837 A | 9/2006 |
| WO | WO-03/090599 | 11/2003 |
| WO | WO-2006/008741 | 1/2006 |

OTHER PUBLICATIONS

International Search Report of Application No. PCT/US2008/001460, Jul. 21, 2008, 4 pages.
Written Opinion of the International Searching Authority, Jul. 21, 2008, 6 pages.
Merrill et al., "Electrical stimulation of excitable tissue: design of efficacious and safe protocols", *Journal of Neuroscience Methods* vol. 141 (2005) pp. 171-198.
Wang et al., "Gastric stimulation in obese subjects activates the hippocampus and other regions involved in brain reward circuitry", *PNAS* vol. 103 No. 42 (Oct. 17, 2006) pp. 15641-15645.
Examination Report for Australian Patent Application No. 2008214349, mailed Jan. 18, 2011, 3 pages.
Examination Report for European Patent Application No. 08713394.8, mailed Jan. 25, 2010, 2 pages.

* cited by examiner

*Primary Examiner* — Carl H Layno
*Assistant Examiner* — Jennifer Ghand
(74) *Attorney, Agent, or Firm* — McDermott Will & Emery LLP

(57) ABSTRACT

Nerves that carry taste sensations to the brain are stimulated in order to diminish (or, depending on the application, augment) the pleasure ordinarily associated with consumption behavior to be modified.

24 Claims, 3 Drawing Sheets

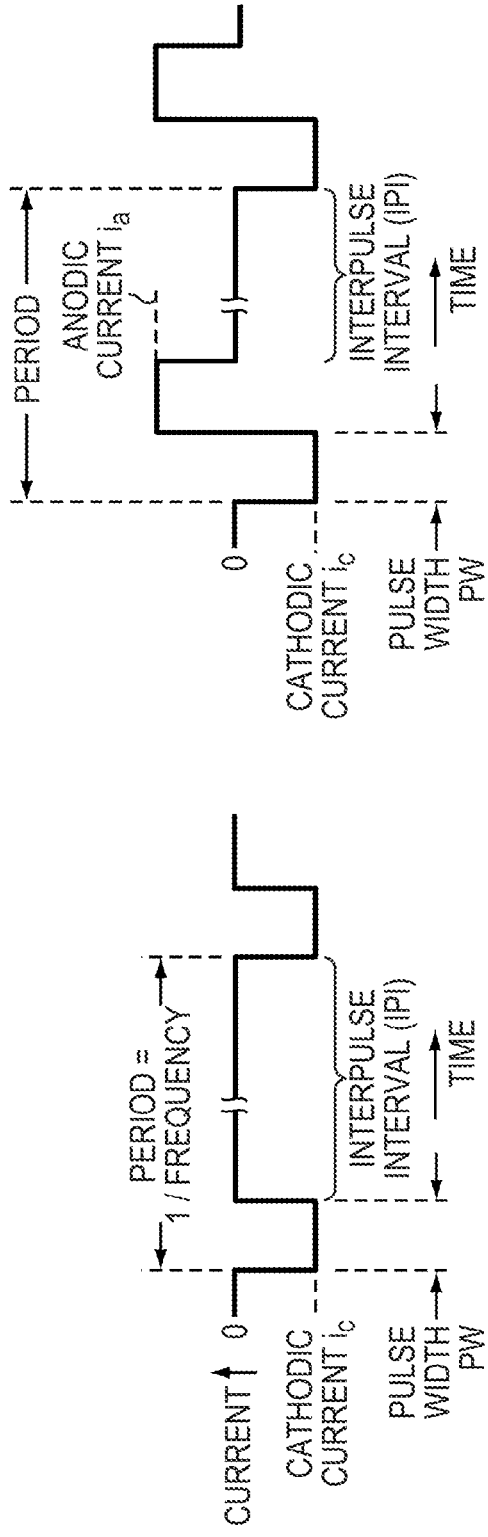
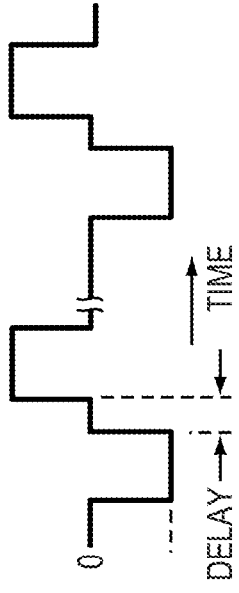
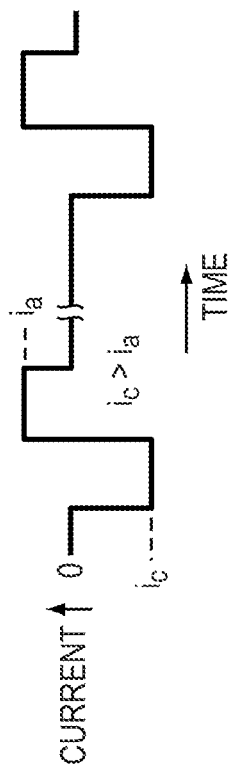
FIG. 1A
FIG. 1B
FIG. 1C
FIG. 1D

TREATMENT OF CONSUMPTION DISORDERS WITH BIOSTIMULATION

RELATED APPLICATION

This application claims the benefit of and priority to U.S. Provisional Application Ser. No. 60/888,124 filed Feb. 5, 2007, the disclosure of which is hereby incorporated by reference in its entirety.

FIELD OF THE INVENTION

The present invention relates to behavioral modification of patients with disorders involving consumption and/or oral gratification, and in particular to systems and methods for treating such disorders.

BACKGROUND

As people become increasingly sedentary, obesity grows as a public health problem. Many people have difficulty preventing their caloric intake from exceeding their energy needs, and as a consequence grow progressively more obese over time. In addition to the psychic impact, obesity shortens lifespan by increasing the incidence of heart disease, diabetes, and possibly cancer. Consequently, individuals spend enormous sums on diets, exercise regimens, and prescription drugs in an attempt to lose weight and/or to maintain a lower weight.

Despite this effort, however, long-term success eludes most would-be dieters. All too many, even if they succeed temporarily in losing weight, return to their previous eating habits and regain the weight they lost. Such people need to modify their eating behavior so that once they succeed in losing weight they do not later regain it.

A similar challenge faces those attempting to quit smoking, drinking, or illicit drug use. In each case, the individual needs assistance in modifying his behavior so that, after an initial effort to quit, he does not slide back into the habits of many years and defeat the progress he has achieved. Attempts at such assistance have included hypnosis and the use of drugs such as disulfiram (commercially sold as Antabuse), which makes alcohol noxious to the user. Hypnosis is clearly impractical on an ongoing, daily basis, while use of drugs raises concerns about side effects and long-term toxicity.

Consequently, there is a continuing need for a way to facilitate modification of behavior so as to maximize the chances of long-term success in overcoming disorders involving consumption of food, drink, tobacco, or illicit drugs (hereafter, "consumption disorders"). Ideally such an approach would be as non-invasive as possible, and could be practiced by the patient herself when and for as long as necessary.

SUMMARY

Embodiments of the present invention treat consumption disorders by helping individuals control their urges to ingest food, drink, tobacco, or illicit drugs. In addition, the invention has been found useful in controlling hiccups, which will therefore be considered a "consumption disorder" for purposes hereof. In various embodiments, the present invention features stimulation of a nerve branch that carries taste sensations to the brain in order to invoke a stimulus that diminishes (or, depending on the application, augments) the pleasure ordinarily associated with the behavior to be modified.

A device in accordance with the invention applies an electrical stimulus to the nerves of the oral cavity, which include the fifth (trigeminal), seventh, ninth, tenth, and twelfth cranial nerves. The stimulus may be applied, e.g., to the hard palate, soft palate and/or tongue. Stimulation of the trigeminal nerve, or facial nerves such as fibers from the Chorda Tympani, may cause the user to perceive any of three sensations: (1) a moderately unpleasant taste that persists for some time after the stimulation ceases, and thereby diminishes the user's desire for oral gratification through eating, drinking, or smoking; (2) a centralized feeling of euphoria; or (3) a feeling of satiety. The sensation experienced by the user depends strongly on the pulsing frequencies, pulse durations, and timing, especially when the frequency and/or duration of the pulse is varied.

For purposes of the present invention, responses (1) and/or (3) are desired. The euphoria response tends to come at higher frequencies between 100 Hz and 300 Hz. It does not have direct relevance to the consumption-related objectives of the present invention, and unlike responses (1) and (3), the euphoria response tends not to linger (it is only experienced during and immediately following stimulation, while satiety tends to last for hours) and is not always consistent—i.e., the experience tends to vary among stimulation sessions.

Embodiments of the present invention facilitate variation of the pulse duration, frequency, and timing, and the range of voltage or current. A device in accordance herewith may be realized in a form sufficiently unobtrusive to be used in a public context, and because the invention avoids the use of drugs, it does not raise toxicity concerns. The approach of the invention can be used in conjunction with an existing diet program or to supplement another product such as appetite-suppressant pills.

A stimulator in accordance with the invention may be constructed from any non-conducting biocompatible material, such as an acrylic plastic, and includes one or more electrodes for applying stimulation within the oral cavity. The electrodes can be made of any conducting biocompatible material, with silver, gold, stainless steel, and platinum being preferred. The electrodes may be sterilizable or disposable. In one embodiment, the stimulator takes the form of a handheld device, at least a portion of which is insertable into a user's mouth and has two, four or a grid of electrodes on a flat surface thereof so that the electrodes may be conveniently brought into contact with the tongue. In another embodiment, the stimulator takes the form of a lollipop or tube of lip balm that the user inserts into his mouth. The stimulator may be adapted to conform to the shape of a user's hard palate, much like the dental retainers used in orthodontia.

Accordingly, in a first aspect, the invention pertains to an apparatus for diminishing a user's desire for oral gratification. In various embodiments, the apparatus comprises least two spaced-apart electrodes for establishing an electric circuit across a portion of a user's body. At least one of the electrodes being configured to contact a surface in the user's oral cavity. The apparatus also comprises circuitry for generating an electrical stimulus across the electrodes. The stimulus elicits a neural response that diminishes the user's desire for oral gratification. The electrical stimulus may comprises a time-varying electrical signal, e.g., a biphasic signal. In some embodiments, the signal has a constant frequency in the 10 Hz-50 Hz range; other embodiments employ a varying frequency ranging from 150 to 300 Hz; from 10 Hz to 50 Hz; or from 10 Hz to 100 Hz. The frequency may vary, for example, over a period of about 4 seconds. The signal may comprise a varying pulse width ranging from 100 μsec to 1 msec, and the pulse width may vary over a period of about 4 seconds. In some embodiments, the signal has a current amplitude ranging from 10 µA to 10 mA.

The apparatus may include a monitoring module for monitoring effects of the signal and altering at least one signal characteristic in response to the monitored effects; and a memory circuit for retaining data characterizing the altered signal. In some embodiments, the monitoring module prevents generation of the electrical simulus until a resistance or impedance threshold across the electrodes is detected. Implementations of the apparatus can include ancillary circuitry implementing features that enhance consumer appeal, e.g., an alarm clock, a calendar, an LCD, a camera, an address book, an MP3 player, and/or a voice note recorder.

In a second aspect, the invention pertains to a method of treating a consumption disorder. In various embodiments, the method comprises applying an electrical stimulus to a surface in the user's oral cavity to elicit a neural response that diminishes the user's desire for oral gratification. The surface may be the hard palate, soft palate and/or tongue. The electrical stimulus may comprise a time-varying electrical signal, e.g., a biphasic signal. In some embodiments, the signal comprises a varying frequency ranging from 150 to 300 Hz; the frequency may vary, for example, over a period of about 4 seconds. The signal may comprise a varying pulse width ranging from 100 µsec to 1 msec, and the pulse width may vary over a period of about 4 seconds. In some embodiments, the signal has a current amplitude ranging from 100 µA to 10 mA. The method may further comprise adapting the signal to a particular user.

BRIEF DESCRIPTION OF THE DRAWINGS

In the drawings, like reference characters generally refer to the same features throughout the different views. Also, the drawings are not necessarily to scale, emphasis instead generally being placed upon illustrating the principles of the invention. In the following description, various embodiments of the present invention are described with reference to the following drawings, in which:

FIGS. 1A-1D illustrate pulse patterns relating to operation of the present invention;

DETAILED DESCRIPTION

1. Operational Principles

Figure 2:
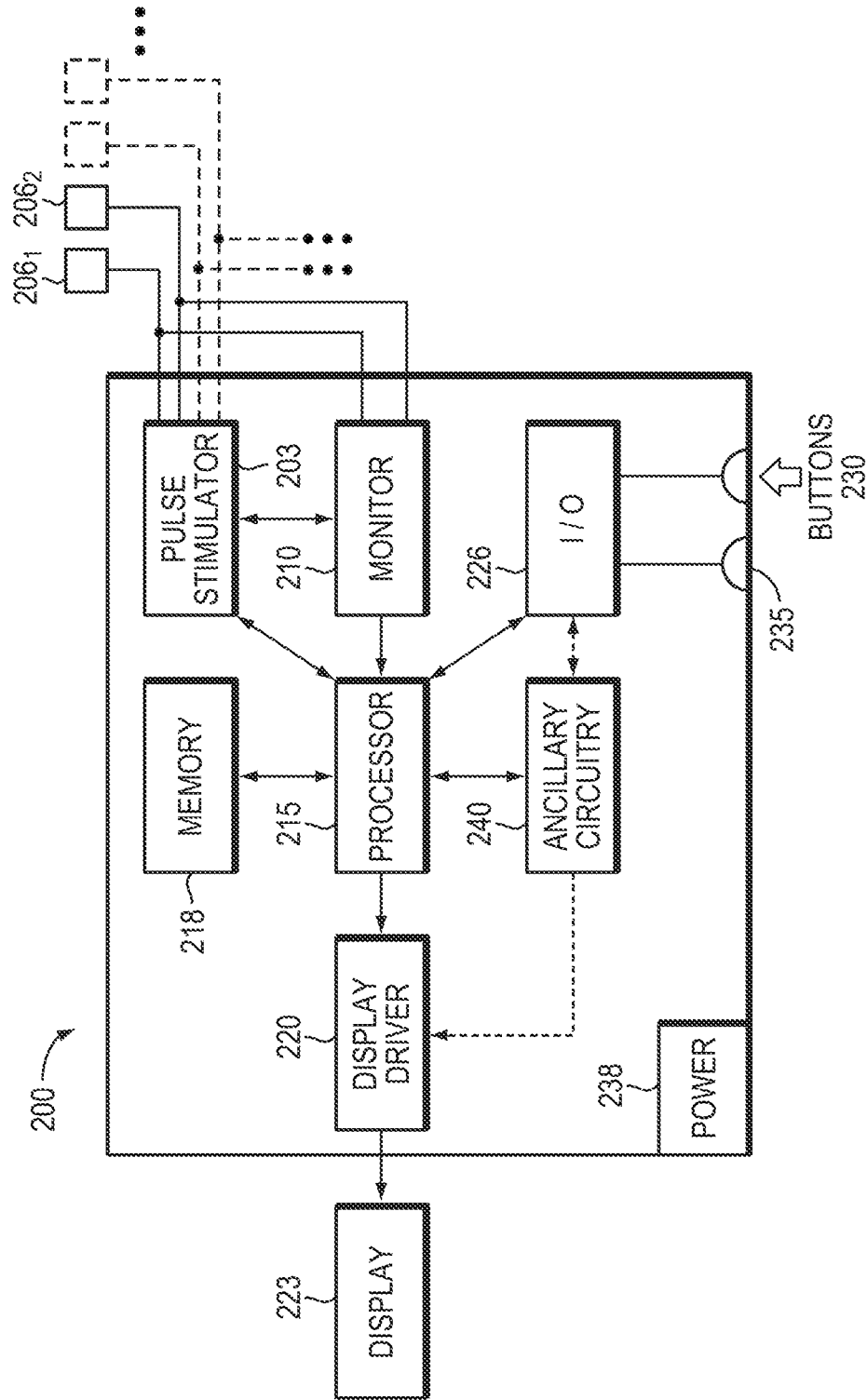
FIG. 2 schematically depicts the components of a biostimulator in accordance with the present invention.

In general, the invention achieves neural potentiation by applying tetanic stimulation, as described, for example, in C. H. Lemon and P. M. Di Lorenzo, *J. Neurophysiol.* 88:2477-2489 (2002); W. O. Wickelgren, *J. Physiol.* 270:115-131 (1977); I. Nussinovitch and R. Rahamimoff, *J. Physiol.* 396: 435-455 (1988); and K. L. Magleby, *J. Physiol.* 234: 353-371 (1973), the contents of these references being incorporated by reference in their entireties. Tetanic stimulation entails delivering a train of stimulating pulses to a nerve at a rate greater than the rate at which the nerve recovers its initial state, resulting in a nonlinear neural response called neural potentiation. In some embodiments, tetanic stimulation is effected by applying a train of pulses having pulse widths and intervals that decrease across the pulse train. In this fashion, the pulses become successively briefer and closer together in time from the beginning to the end of the pulse train, which potentiates the neural response to the stimuli. As explained below, the optimal parameters for electrical stimulation can be readily ascertained, even automatically, with minimal experimentation.

The pulse train can involve a train of current pulses or a train of voltage pulses conforming to a desired profile. Preferred pulse widths range from about 1 µsec to about 10 sec, and more preferably from about 100 µsec to 1 msec, with 500 µsec being typical; the range 1-100 µsec has also shown promise. The pulse repetition frequency—i.e., the number of pulses per second—is generally below 100 Hz, typically in the 10-50 Hz range. However, higher frequencies, in the range of 100 Hz-500 Hz, may also be useful.

We have found that modifying the pulse width and/or modifying the pulse repetition frequency during stimulation, especially at these higher frequencies, results in greater intensity and more noticeable central effects. In particular, we have found that the effect is greatly accentuated when the frequencies are varied from 150 to 300 Hz and back to 150 Hz, e.g., over a period of 1 sec to 10 sec, preferably 4 seconds. We have also found that the effect is accentuated when the pulse widths are varied from short to long and back to short again (e.g., 100 µsec to 1 msec and back to 100 µsec), e.g., over a period of 1 sec to 10 sec. Varying the pulse width while either maintaining a constant frequency or also varying frequencies tends to affect gut motility and gives the user the feeling of satiation resulting in a decrease in the physical desire to eat.

In one exemplary stimulation pattern, a 25 Hz pulse is applied for 1 second (i.e., 25 pulses); no pulses are applied for 1 second; a 25 Hz pulse is applied for 1 second; and again no pulses are applied for 1 second. This pattern is repeated for the entire stimulation session (e.g., 20-30 seconds). This general approach is appropriate for stimulations using constant frequency, constant pulse width, varying frequency and/or pulse width. It is based on the fact that neurons fire in volleys of action potentials, separated by rest periods.

The optimal pulse amplitude depends on the number and size(s) of the electrodes used (which, in turn, determines the charge or current density). Preferred working voltages range from about 1 µV to about 50 V, with more preferred voltages between about 1 mV and 10 V, and with especially preferred voltages ranging from about 5 to about 10 V. A preferred working current range is about 100 µA to about 10 mA; in broad terms, 250 µA is the threshold for causing an effect or feeling it, while 4 or 5 mA is the threshold of pain. But these parameters depend strongly on the number, location and size(s) of the electrodes and the mass of the user's tongue. Lower frequencies cause less pain at higher amplitudes. We have found that with four electrodes having a diameter of 7 mm and configured in a 2×2 grid pattern spaced 1 inch apart, the tongue begins to twitch (indicating that muscle spindles are contracting) at amplitudes above 3.5 mA. This will vary according to the physiology of different users' tongues.

For ease of explanation, the ensuing discussion will focus on current pulsing, in which a current source applies a current across one or more electrode pairs in accordance with the desired pulse profile; it should be understood, however, that the same principles apply to voltage pulsing. In monophasic pulsing, illustrated in FIG. 1A, a constant current is passed for a period of time (generally on the order of tens to hundreds of microseconds), and then the external stimulator circuit is open-circuited (i.e., effectively removed electrically from the electrodes) until the next pulse. In biphasic pulsing, a constant current is passed in one direction, then the direction of current is reversed, and then the circuit is open-circuited until the next pulse. In biphasic pulsing the first phase, or stimulating phase, is used to elicit the desired physiological effect such as initiation of an action potential, and the second phase, or reversal phase, is used to reverse electrochemical processes occurring during the stimulating pulse. The reversal phase helps reverse conditions that can damage tissue and the metal electrodes. For this reason, monophasic pulsing is most efficacious for stimulation, but is not as safe (in terms of avoiding tissue damage) as biphasic pulsing; see D. R. Merrill et al., *J. Neurosci. Meth.* 141:171-198 (2005). Accordingly, biphasic pulsing is preferred for the present invention, although monophasic pulsing may be useful in some applications.

It is common to use a cathodic pulse as the stimulating phase (as illustrated in FIGS. 1A-1D, with current going negative during the pulse), followed by an anodic reversal phase, although anodic pulsing may also be used for stimulation. The frequency of stimulation is the inverse of the period, or time between the start of two consecutive pulses, each of which have a pulse width PW. The interpulse interval (IPI) is the period of time between the end of one pulse and the start of the next pulse.

FIG. 1B illustrates charge-balanced biphasic pulsing, where the charge in the stimulation phase equals the charge in the reversal phase. FIG. 1C illustrates charge-imbalanced biphasic pulsing in which there are two phases, but the charge in the stimulation phase is greater than the charge in the reversal phase. Charge-imbalanced biphasic waveforms reduce unrecoverable charge in the cathodic direction and in the anodic direction. They help minimize damage to either the stimulated tissue or the metal electrode. FIG. 1D illustrates the use of an interphase delay between the stimulation phase and the reversal phase. The delay addresses the possibility in biphasic pulsing that the reversal phase can defeat some of the desired physiological effects of the stimulation phase (thereby increasing the threshold required for stimulation of the nerve). The delay (100 μsec is typically sufficient) reduces this threshold to a level near that of monophasic pulses.

Various parameters may be varied to tailor the output pattern to a particular user or, for a particular user, to prevent the user's neurons from becoming acclimated (and therefore possibly less responsive) to the stimulation. Parameters may be varied during each single use and/or between uses. The varied parameters may include the pulse width and the pulse repetition frequency.

In order to prevent initial "shock" when the device is first applied, power output may be ramped up over a time interval of several pulses to several seconds to "ease" the user into the stimulation. It may also be desirable to incorporate an initialization or configuration procedure, whereby the user can set the comfortable maximum power level of the pulses. This may be accomplished by slowly ramping up the power output while the user applies the device. At the point where the output begins to become uncomfortable, the user can remove the device, which will record the output level to memory. The device may also be configured to monitor the frequency of use and to reduce or limit the output power—or even disable the output altogether—to prevent injury.

2. Representative Configuration

FIG. 2 is a generalized representation of a circuit architecture 200 implementing functionality in accordance with the present invention. The various components are shown conceptually to indicate their roles and interaction, but this is for explanatory purposes only; it should be understood that other computational configurations (e.g., using a bidirectional bus to facilitate communication among components) are within the scope of the disclosure.

The circuit 200 includes a pulse stimulator 203, which drives at least one pair of external electrodes representatively illustrated at $206_1$, $206_2$. A monitoring circuit 210 is connected to the electrodes and monitors the voltage and/or current across the electrodes 206. Monitoring circuit 210 may also keep track of derived parameters such as the impedance of the tissue (e.g., the tongue) across the electrodes 206. Monitor circuit 210 typically performs basic feedback functions such as ensuring that output parameters are not exceeded or that the voltage or current across the electrodes 206 conforms to expectations. In addition, circuit 210 can sense conditions that facilitate automatic operation with minimal user action. Circuit 210 may, for example, detect use of the device when resistance across the electrodes 206 drops to a point indicative of contact with the user's tongue and activate the pulse stimulator. Circuit 210 may also, for example, detect poor electrical contact with the user's tongue or the removal of the device from the user's tongue due to increased resistance across the electrodes 206, and deactivate the pulse stimulator and/or inform the user of poor electrical contact through an audio, visual, or other feedback mechanism. Similarly, during calibration (as described below), circuit 210 may detect removal of the electrodes 206 from the user's tongue, indicating that the user's tolerance level has been reached and that the current output parameters should be stored as maximum limits.

In some embodiments, monitoring circuit 210 is part of pulse stimulator 203, while in other embodiments it is a separate, dedicated circuit that includes, for example, an analog comparator, a thresholding circuit or trigger, and a computational module for calculating derived parameters. The monitoring circuit 210 may also store values corresponding to a maximum safe current or voltage and to a minimum current or voltage indicating that the device has been put into use.

A microprocessor 215 controls the overall operation of the circuit 200. Programming for processor 215 resides in a non-rewritable portion of a memory circuit 218. The memory circuit 218 may contain volatile (e.g., random access) memory for scratchpad use by processor 215 during operation and to support input/output functions; and non-volatile (e.g., Flash or microdisk) memory to store user-specific parameters defined during operation. The memory circuit 218 may be incorporated within the microprocessor itself or in a separate circuit. Processor 215 also controls a display driver 220, which dictates the appearance of, and information displayed on, an external display 223. One or more input/output (I/O) modules 226 send signals to and receive signals from external controls (e.g., a series of buttons 230) or via one or more I/O ports (e.g., a USB port 235, a headphone jack, etc.). The circuit 200 is powered by a power source 238. Optional ancillary circuitry 240, described in greater detail below, can supplement the basic functionality of the invention and/or provide unrelated capabilities that enhance the appeal of the device. In some instances or for some functions, ancillary circuitry 240 may communicate directly with or through I/O module(s) 226 and with display driver 220, bypassing processor 215.

Figure 3:
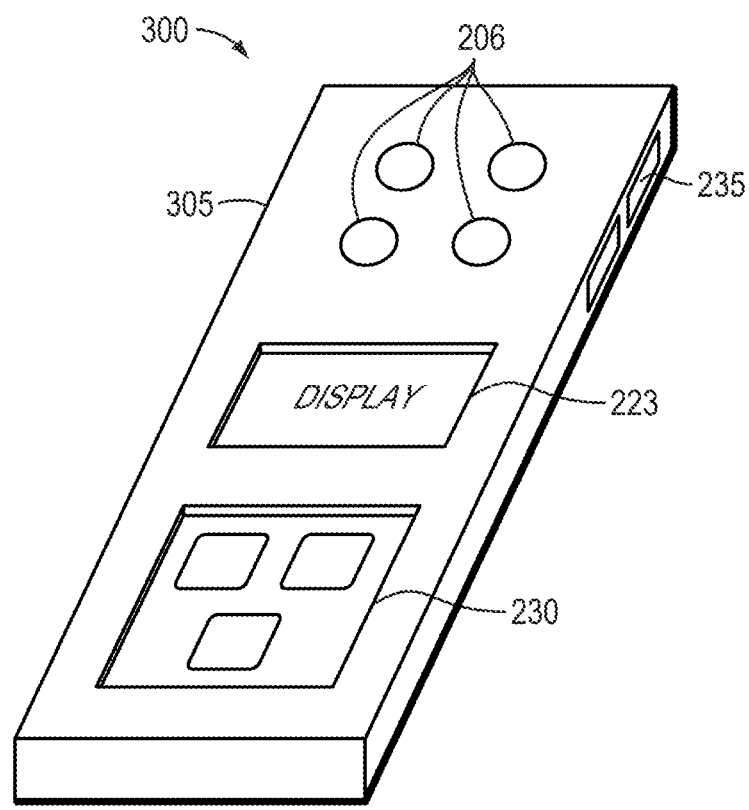
FIG. 3 is a perspective view of a handheld device in accordance with the invention.

The manner in which the circuit 200 may be realized in a working device is illustrated in FIG. 3. The circuit 200 is contained within a housing 305 that is configured for convenient insertion into a user's mouth so that the four electrodes 206 may be brought into contact with the tongue. The display 223 can show status information relating to operation of the invention; for example, the display 223 may be a liquid-crystal display (LCD) that shows reminders to utilize the device at appropriate times. (An audio transducer that emits an audible alarm may also be included.) Depending on the ancillary circuitry 240 included in the design, display 223 may also show information relating to ancillary functions of the device.

Buttons 230 allow the user to control operation of the device, but as discussed below, it is preferred for the circuit 200 to be programmed so as to operate automatically based on conditions sensed by monitoring circuit 210. Accordingly, the number of buttons 230 dedicated to the functionality of the invention is preferably minimized, leaving room for buttons (and/or other I/O devices such as trackballs, slide controls, click wheels, etc.) dedicated to ancillary circuitry.

Other configurations for housing 305 are possible. For example, housing 305 may have the form factor of a lipstick or lip-balm tube. Alternatively, it is possible to separate the various components into multiple housings. For example, electrodes 206 may reside on a lollipop-shaped fixture connected, via a cable, to a belt-worn housing containing circuitry 200. Since the belt-worn housing can be relatively large, a bigger power supply and more substantial ancillary circuitry can be included. The lollipop-shaped fixture may be disposable or have a disposable head that is easily removed and replaced.

Components of circuitry 200 may also be divided into separate sections within a single housing 305. For example, the components responsible for stimulation-related functions may be arranged in one portion of circuit 200 and all other components arranged in a separate physical section; this bifurcated design enables simpler deployment of new functions and device revisions, potentially simplifying FDA approval for such changes. Circuitry 200 can even be incorporated in a retainer, mouthguard, piercing, or other device that remains in the oral cavity to enable the user to wear the stimulator continuously (and even be automatically stimulated at regular intervals).

With renewed reference to FIG. 2, pulse stimulator 203 comprises a conventional signal generator capable of generating the current or voltage pulses described above. The output is desirably protected against short circuits. Furthermore, the electrode potential should be kept within bounds that prevent irreversible Faradaic reactions from occurring at levels intolerable to the physiological system or to the electrode. If irreversible Faradaic reactions do occur, they must be tolerable physiologically and to the electrodes, i.e., their detrimental effects must be low in magnitude; for example, if corrosion occurs but at a very slow rate, the electrode will be long-lasting.

Processor 215 controls the operation of pulse stimulator 203 based on parameters stored in memory 218. The proportionate degree of control exercised by processor 215 and pulse stimulator 203 represents a routine design choice. In some embodiments, pulse stimulator 203 is equipped to generate pulse patterns based on input parameters specifying the shape of the pulse train, the repetition frequency (both of which, as noted above, may vary), and the amplitude. In other embodiments, pulse stimulator 203 is a simple current or voltage source (or a power supply capable of operating in either mode), and processor 215 operates as a microcontroller directly governing its output by sending a series of switching bit signals, conforming to the desired pulse pattern, that turn the power on or off. Biphasic pulse patterns can be implemented by utilizing one of the above embodiments with a "push-pull" output topology.

In a preferred embodiment, power source 238 typically comprises one or more batteries that are optionally rechargeable. For example, power source 238 may include circuitry that inductively couples to a charging cradle in which the housing 305 resides when not in use, much like the wireless charging system used for electric toothbrushes. This permits the device 300 to be fully waterproof, allowing for thorough cleaning following use. Moreover, the charging cradle (or the device 300 itself) may incorporate an ultraviolet (UV) sterilization system utilizing UV lamps or UV LEDs, facilitating sterilization between uses.

As noted above, the size of the electrodes determines the charge or current density actually delivered to the user. In general, it is found that nerves are sufficiently widespread on the tongue that exact placement of the electrodes is not critical. The anterior (forward) portion of the tongue tends to be more sensitive than the middle or posterior portion. Accordingly, the number and configuration of electrodes 206 may be tailored to particular designs. In one approach, a single electrode makes contact with the user's oral cavity and a counter-electrode is deployed elsewhere on the user's body (e.g., looped around a wrist) or connected to grounding within circuit 200. Alternatively, two, four or a grid of 9 or more electrodes configured for oral contact may be used, depending on the application. For example, different electrode pairs within the grid may each constitute a channel separately addressable by pulse stimulator 203, which, in turn, may drive different channels with different pulse parameters, including but not limited to pulse amplitude, pulse frequency, pulse width, and pulse timing in order to vary the stimulator pattern experience by the user (e.g., to avoid acclimation). In a ring configuration, a round central electrode is surrounded by an annular conductive ring serving as the return path for current, with a nonconducting annular gap between the two conductive regions.

In some embodiments, housing 305 includes a retraction mechanism enabling the user to retract the electrodes into the device between uses to keep them clean and protected. Alternatively, the device may also incorporate a removable cap that fits over the electrodes and serves the same purpose.

In general, the electrodes can be made of any conducting biocompatible material, with silver, gold, stainless steel, and platinum being preferred metals. However, it is also possible to use carbon or another non-metal material, e.g., a conductive ink printed onto a thin, flexible substrate. Such a substrate can also facilitate electrode retraction as described above. Non-ferrous conductive materials such as tungsten, gold or platinum/platinum-iridium can be used for stimulation during magnetic resonance imaging (MRI) and functional MRI (FMRI) studies. The lengths of non-ferrous electrodes may be extended over several feet so that the device's electronics can be located outside the magnetic field of the MRI bore. Alternately, non-ferrous electrodes may be coupled to a fiber-optic signal-transmission system operable over several feet for the same purpose. More generally, the electrodes may be designed to be disposable, easily replaced in the device, and/or single-use.

Electrodes may also be contained within a cartridge, which is loaded into the device 300. The cartridge may, for example, contain enough disposable or single-use electrodes to last the user for a day, week, etc. The cartridge may be integrated into housing 305 and configured to dispense single electrodes when needed. This approach permits the use of electrodes deposited onto a substrate as a printed pattern that dissolves or washes away after a single use due to contact with saliva. Single-use electrodes may, if desired, incorporate a breath-freshening solution in the electrode substrate or a mildly-noxious tasting solution that alters the taste of food (enhancing the noxious taste created by the stimulation).

Electrodes may also be designed to fail after a predetermined amount of usage. For example, the electrode failure can be dictated by the number of applications (e.g., 50 stimulations) or a time duration (e.g., 1 week). This may be accomplished, for example, through the use of circuitry on the electrode that disrupts current flow to the electrodes or a fuse on the electrode that can be blown to prevent current flow thereto.

Ancillary circuitry 240 may provide additional capabilities related to the function of the device 300 and/or functions unrelated to biostimulation but which nonetheless enhance consumer appeal. In particular, individuals today carry an increasing number of portable electronic devices—cellphones, personal music players, personal digital assistants (PDAs), BLACKBERRY communication devices, for example—and persuading consumers to tote yet another device can be challenging. Accordingly, by adding functionality associated with such unrelated devices, the present invention can avoid imposing an extra burden by replacing a device the user would carry anyway. For example, ancillary circuitry may provide alarm clock (which may include reminder alarms to apply biostimulation, as noted above), calendar and contacts/address book functions enabled through display 223; an MP3 player enabled via display 223, a headphone/earbud jack connected to I/O module 226, and Flash memory in memory module 218 to store music files; and/or a voice note recorder enabled via an integrated microphone or microphone jack connected to I/O module 226 and Flash memory in memory module 218 to store recordings. Circuitry implementing such functions is readily available and conventional in the art.

Viewed as a personal health device, the present invention can be combined with other health-related functions. Ancillary circuitry 240 may therefore include a pedometer that counts the user's steps throughout the day, and displays this information to the user via display 223. Alternatively or in addition, ancillary circuitry 240 may include a calorie counter that helps the user record his dietary intake throughout the day and the time at which he ate. The calorie counter may employ a database, stored in memory 218, with the typical caloric content of common food; the database may be accessed via buttons 230 that operate menus displayed on display 223. A heart-rate meter implemented in ancillary circuitry 240 enables the user to measure and record her heart rate, while a glucose meter enables diabetic users to monitor their glucose levels. The data gathered by the pedometer, calorie counter, and heart-rate meter may be processed by onboard health software stored in memory 218 to provide the user with overall health information that is directly related to success in using the biostimulation features of the invention. Once again, functionality implementing these functions is conventional and straighforwardly implemented by those of skill in the art.

Moreover, a USB port 235 can permit the user to transfer health-related information gathered by the device 300 to an external computer, where more elaborate software can track the user's progress and integrate the data into a broader presentation or monitoring functions. This may include usage tracking functionality, whereby the time of day, duration, power level, etc. of each stimulation is recorded and provided to the external computer.

Alternatively, the circuit 200 may be adapted to fit within an existing device, such as a digital camera or a cellphone, effectively enhancing the appeal of that device by providing the biostimulation functions described herein.

3. Device Operation

As noted above, a nonvolatile portion of memory 218 contains instructions executed by processor 215 to implement the functions of the invention via pulse stimulator 203 and electrodes 206. In particular, the instructions typically reflect one or more pre-programmed settings that cause delivery of stimulation according to specified program of pulse durations, repetition frequencies, amplitude, and number of electrodes turned on or off. Typically, the instructions also cause processor 215 to continually process data from monitor circuit 210 in order to turn the device on when electrodes 206 encounter the buccal cavity and ensure proper operation of the device during use—i.e., preventing excessive pulse amplitude should the impedance across the user's tongue unexpectedly decrease, or increasing the amplitude and/or activating additional electrodes if the impedance increases. The instructions may cause stimulation to occur for a pre-set amount of time (e.g., 20 seconds) or, alternatively, allow simulation to persist for as long as the electrodes are applied to the user's buccal cavity.

Processor 215 can also be programmed to change the stimulus parameters (current, voltage, pulse duration, pulse interval, repetition frequency, etc.) according to the history of stimuli it has delivered. For example, the magnitude of the pulse voltage or current may be increased (to overcome desensitization) or decreased (to prevent overuse, e.g., if the user has used the stimulator 300 more than a certain number of times in a specified period).

Although the appropriate stimulus parameters tend not to vary significantly among users, there may be some variation; for example, some users may experience discomfort at commonly acceptable pulse amplitudes, while others may require greater stimulation. Accordingly, the executable instructions may implement a calibration routine actuated by one of the buttons 230. The user holds the electrodes 206 against the tongue or other buccal tissue as the pulse amplitude is increased, and removes the electrodes when the user's tolerance level has been reached. The calibration routine records the pulse amplitude at removal as a maximum limit. Furthermore, the maximum tolerable pulse amplitude may be correlated with other stimulation parameters (according to modeling equations or as database entries), so that setting the amplitude tailors the stimulation program to the user.

Calibration may be integrated with monitoring functions and continue during use. For example, if monitoring circuit 210 detects that the user is retaining the electrodes against his tongue for an increasing amount of time, the calibration routine may interpret this as acclimation and alter the stimulation parameters accordingly. As stated earlier, it is desirable for the calibration routine to require minimal user participation and instead infer the need for program changes based on the user's natural operation of the device.

The need may arise to alter from time to time the operating instructions stored in memory 218. This may be accomplished via the USB port 235, with the device 300 connected to the user's computer. The user visits a website having a link to replacement software and downloads this into memory 218 in a conventional fashion.

It should be emphasized that the operating instructions for processor 215 may be written in any one of a number of high-level languages, such as FORTRAN, PASCAL, C, C++, C#, Java, Tcl, or BASIC; in a script, macro, or functionality embedded in commercially available software, such as EXCEL or VISUAL BASIC; but more conventionally is implemented in an assembly language directed to the processor 215.

While the invention has been particularly shown and described with reference to specific embodiments, it should be understood by those skilled in the art that various changes in form and detail may be made therein without departing from the spirit and scope of the invention as defined by the appended claims. For example, it is possible to implement the stimulator circuitry in analog only, without digital components such as a microprocessor, etc. The scope of the invention is thus indicated by the appended claims and all changes which come within the meaning and range of equivalency of the claims are therefore intended to be embraced.

What is claimed is:

1. An apparatus for diminishing a user's desire for oral gratification, the apparatus comprising:
   (a) at least two spaced-apart electrodes for establishing an electric circuit across a portion of a user's body, at least one of the electrodes being configured to contact a surface in the user's oral cavity; and
   (b) circuitry configured to generate, across the electrodes, an electrical signal comprising a train of pulses having a width that is varied over time during a single application of the signal to the surface in the user's oral cavity, the signal eliciting a neural response that diminishes the user's desire for oral gratification, wherein the train comprises some pulses having a first width and other pulses having a second width different from the first, and the pulse-widths vary from the first width to the second width and back to the first width during a single application of the signal.

2. The apparatus of claim 1, wherein each electrode is constructed of a metal selected from the group consisting of silver, gold, stainless steel, and platinum.

3. The apparatus of claim 1, wherein the signal is biphasic.

4. The apparatus of claim 1, wherein the signal comprises a varying pulse width ranging from 100 μsec to 1 msec.

5. The apparatus of claim 4, wherein the pulse width varies over a period of about 4 seconds.

6. The apparatus of claim 1, wherein the signal has a current amplitude ranging from 10 μA to 10 mA.

7. The apparatus of claim 1, wherein the electrodes are fabricated from a sterilizable biocompatible material.

8. The apparatus of claim 1, further comprising a monitoring module for monitoring effects of the signal and altering at least one signal characteristic in response to the monitored effects.

9. The apparatus of claim 8, further comprising a memory circuit for retaining data characterizing the altered signal.

10. The apparatus of claim 8, wherein the monitoring module prevents generation of the electrical signal until a resistance or impedance threshold across the electrodes is detected.

11. The apparatus of claim 1, further comprising a housing for supporting at least two electrodes on an external portion thereof, the external portion being configured for insertion into the user's oral cavity.

12. The apparatus of claim 1, further comprising ancillary circuitry implementing at least one of an alarm clock, a calendar, an LCD, a camera, an address book, an MP3 player, and a voice note recorder.

13. The apparatus of claim 1, wherein the first width is less than the second width.

14. The apparatus of claim 1, wherein the first width is 100 microseconds and the second width is 1 millisecond.

15. The apparatus of claim 14, wherein the signal has a duration of between 1 and 10 seconds.

16. A method of treating a consumption disorder, the method comprising applying an electrical signal to a surface in a user's oral cavity to elicit a neural response that diminishes the user's desire for oral gratification, the signal comprising a train of pulses having a width that is varied over time during a single application of the signal to the surface in the user's oral cavity, wherein the train comprises some pulses having a first width and other pulses having a second width different from the first, and the pulse-widths vary from the first width to the second width and back to the first width during a single application of the signal.

17. The method of claim 16, wherein the surface is at least one of the hard palate, soft palate, or tongue.

18. The method of claim 16, wherein the signal is biphasic.

19. The method of claim 16, wherein the signal comprises a varying pulse width ranging from 100 μsec to 1 msec.

20. The method of claim 19, wherein the pulse width varies over a period of about 4 seconds.

21. The method of claim 16, wherein the signal has a current amplitude ranging from 10 μA to 10 mA.

22. The method of claim 16, further comprising the step of adapting the signal to a user.

23. The method of claim 16, wherein the first width is less than the second width.

24. The method of claim 16, wherein the first width is 100 microseconds and the second width is 1 millisecond.

* * * * *